United States Patent [19]

Kuberasampath et al.

[11] Patent Number: 5,162,114

[45] Date of Patent: Nov. 10, 1992

[54] BONE COLLAGEN MATRIX FOR XENOGENIC IMPLANTS

[75] Inventors: Thangavel Kuberasampath, Medway; Richard J. Ridge, Acton, both of Mass.

[73] Assignee: Stryker Corporation, Kalamazoo, Mich.

[21] Appl. No.: 616,374

[22] Filed: Nov. 21, 1990

Related U.S. Application Data

[60] Division of Ser. No. 422,613, Oct. 17, 1989, Pat. No. 4,975,526, which is a continuation-in-part of Ser. No. 315,342, Feb. 23, 1989, Pat. No. 5,011,691.

[51] Int. Cl.$^5$ ............... A61K 37/12; A61F 2/00; C07K 13/00; C12P 21/00
[52] U.S. Cl. ............... 424/423; 424/424; 424/426; 523/113; 128/DIG. 8
[58] Field of Search .......... 424/423, 424, 426; 523/113; 530/356, 350, 401, 412, 427, 840; 128/DIG. 8

[56] References Cited

U.S. PATENT DOCUMENTS

| | | | |
|---|---|---|---|
| 4,172,128 | 10/1979 | Thiele et al. | 424/95 |
| 4,394,370 | 7/1983 | Jeffries | 514/21 |
| 4,563,350 | 1/1986 | Nathan et al. | 424/95 |
| 4,563,489 | 1/1986 | Urist | 514/21 |
| 4,725,671 | 2/1988 | Chu et al. | 530/359 |
| 4,789,663 | 12/1988 | Wallace et al. | 514/21 |
| 4,795,467 | 1/1989 | Piez et al. | 623/16 |
| 4,812,120 | 3/1989 | Flanagan et al. | 433/173 |

FOREIGN PATENT DOCUMENTS

| | | |
|---|---|---|
| 0069260 | 6/1982 | European Pat. Off. |
| 0148155 | 2/1985 | European Pat. Off. |
| 0170979 | 7/1985 | European Pat. Off. |
| 0182483 | 8/1985 | European Pat. Off. |
| 0169001 | 1/1986 | European Pat. Off. |
| 0230647 | 12/1986 | European Pat. Off. |
| 0212474 | 4/1987 | European Pat. Off. |
| 0309241 | 3/1989 | European Pat. Off. |
| 8600526 | 1/1986 | PCT Int'l Appl. |
| 8800205 | 1/1988 | PCT Int'l Appl. |
| 2178447 | 11/1987 | United Kingdom |

OTHER PUBLICATIONS

Reddi, "Cell Biology and Biochemistry of Endochondral Bone", Coll. Res., vol. 1:209-226.

Sampath et al., Proc. Natl. Acad. Sci. USA, vol. 78, No. 12, pp. 7599-7603, "Dissociative Extraction and Reconstitution . . . ".

Sampath et al., Proc. Natl. Acad. Sci. USA, vol. 80, pp. 6591-6595, "Homology of Bone-inductive Proteins from Human, Monkey, Bovine . . . ".

Deatherage et al., Collagen Rel. Res., vol. 7/1987, pp. 225-231, "Packaging and Delivery of Bone Induction . . . ".

Deatherage et al., Int. J. Oral Maxillofac. Surg., vol. 17/1988, pp. 395-399, "A Review of Matrix-Induced Osteogenesis . . . ".

Spector, J. Arthroplasty, vol. 2/1987, pp. 163-177, "Historical Review of Porous-coated Implants".

Strand et al., Biotech. Bioeng., vol. 26/1984, pp. 503-507, "A Modified Matrix Perfusion . . . ".

Aspenberg et al., J. Bone Joint Surg., vol. 70/1988, pp. 625-627, "Hydroxyapatite-Coated . . . ".

Glowacki et al., The Lancet, 1981, pp. 959-963, "Application of the Biological Principle of Induced . . . ".

Urist et al., Clin. Orthoped. Rel. Res., vol. 187/1984, pp. 277-280, "$\beta$-tricalcium Phosphate Delivery System . . . ".

Cook et al., Clin. Orthoped. Rel. Res. vol. 232/1988 pp. 225-243 "Hydroxyapatite-Coated Titanium . . . ".

*Primary Examiner*—Nathan M. Nutter
*Attorney, Agent, or Firm*—Testa, Hurwitz & Thibeault

[57] ABSTRACT

Disclosed is a matrix material for implantation in a mammalian host comprising biocompatible mineral-free type I bone collagen, xenogenic to the host, and biodegradable therewithin. The matrix is manufactured from protein-extracted bone powder treated with certain swelling agents to increase its surface area and porosity. The matrix may be combined with osteogenic protein to induce reliably and reproducibly endochondral bone formation. It also can be used as a surface coat around implantable prosthetic devices to promote cellular ingrowth or as a carrier for sustained release of various therapeutic compositions.

15 Claims, 8 Drawing Sheets

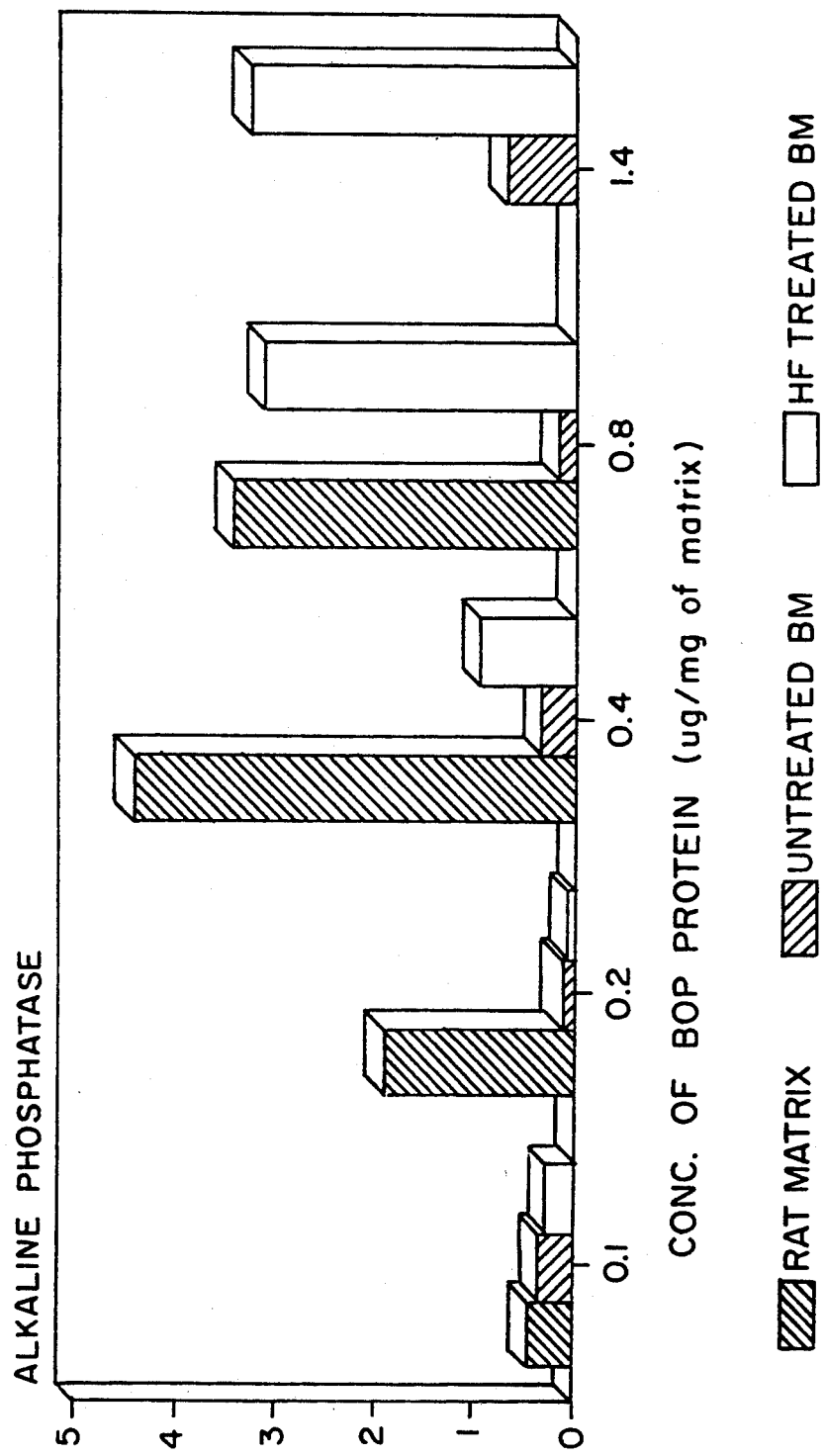

BONE COLLAGEN MATRIX FOR XENOGENIC IMPLANTS

REFERENCE TO RELATED APPLICATIONS

This is a division of application Ser. No. 422,613, filed Oct. 17, 1989 and now U.S. Pat. No. 4,975,526, which is a continuation-in-part of copending U.S. application Ser. No. 315,342 filed Feb. 23, 1989 entitled Osteogenic Devices and now U.S. Pat. No. 5,011,691, the disclosure of which is hereby incorporated by reference.

BACKGROUND OF THE INVENTION

This invention relates to a biocompatible, implantable material which is absorbed naturally in vivo with minimal immunological reaction, and to the methods for its production. More particularly, this invention relates to a superior collagenous bone matrix useful as a xenogenic implant for use as an osteogenic device, as a bone particle coating for implantable prostheses, as a delivery vehicle for the in vivo sustained release of protein, and as a scaffold for anchorage-dependent cells.

A biocompatible, implantable material that can be resorbed in vivo could be used to promote conductive bone growth, induce osteogenesis when combined with an osteoinductive protein, provide a substratum for in vivo or in vitro growth of anchorage-dependent cells, or serve as a carrier for the sustained release of, for example, a therapeutic drug or antibiotic. Such a material must be biocompatible, that is, not induce an immunogenic/inflammatory response in vivo. Its physical structure must allow cell infiltration, and it must have an in vivo resorption time appropriate for its function.

The potential utility of an osteogenic device capable of inducing endochondral bone formation in vivo has been recognized widely. It is contemplated that the availability of such a device would revolutionize orthopedic medicine, certain types of plastic surgery, and various periodontal and craniofacial reconstructive procedures.

The developmental cascade of bone differentiation in mammalian bone tissue is well documented in the art (Reddi, 1981, *Collaoen Rel. Res*, 1:209-226. Though the precise mechanisms underlying the phenotypic transformations are unclear, it has been shown that the natural endochondral bone differentiation activity of bone matrix can be dissociatively extracted and reconstituted with inactive residual collagenous matrix to restore full bone inducing activity (Sampath et al., 78 *Proc. Natl. Acad. Sci. USA* 7599-7603 (1981). Recently, the protein factors hereafter referred to as osteogenic Protein (OP) responsible for inducing osteogenesis have been purified, expressed in recombinant host cells, and shown to be truly osteoinductive when appropriately sorbed onto a matrix. (U.S. Pat. application No. 179,406).

Studies have shown that while osteoinductive proteins are useful cross species, the demineralized bone matrix heretofore required for inducing endochondral bone formation is species specific (Sampath and Reddi (1983) PNAS 80:6591-6594). Implants of demineralized, extracted xenogenic bone matrix and OP invariably have resulted in a strong inflammatory response that has inhibited osteogenesis, presumably due to immunogenic protein components in the bone matrix. Hence, successful osteoinduction to date has required the use of allogenic bone matrix. This restriction on osteogenic devices is a serious limitation with respect to human clinical use, as human bone is neither readily available nor cost effective.

EPO 309,241 (published Mar. 29, 1989, filed Sep. 22, 1988, priority Sep. 25, 1987) discloses a device for inducing endochondral bone formation comprising an osteogenic matrix extract, and a matrix carrier comprising 60-90% mineral component and 2-40% collagen.

U.S. Pat. No. 4,563,350, published Jan. 7, 1986, discloses a xenogenic osteogenic device comprising a bone-inducing extract that had been purified by gel filtration and ion exchange chromatography, and a collagenous matrix composed of approximately 90% trypsinized bovine bone matrix and 10% bovine dermal collagen. Endochondral bone formation is said to require the presence of at least 10-15% dermal collagen in the disclosed matrix.

Deatherage et al., (1987) *Collagen Rel. Res.* 7:2225-2231, purport to disclose an apparently xenogenic implantable device comprising a bovine bone matrix extract that has been minimally purified by a one-step ion exchange column and highly purified human Type-I placental collagen.

The current state of the art of materials used in surgical procedures requiring conductive bone repair, such as the recontouring or filling in of osseous defects, is disclosed by Deatherage (1988) *J. Oral Maxillofac. Suro.* 17:395-359. All of the known implant materials described hydroxylapatite, freeze-dried bone, or autogenous bone grafts) have little or no osteoinductive properties. Clearly, the ability to induce osteogenesis is preferred over bone conduction for most procedures. Even when bone conduction is the indicated procedure for bone repair, a matrix consisting of non-immunogenic, extracted, xenogenic bone collagen heretofore has not been developed.

U.S. Pat. No. 4,795,467 discloses a bone repair composition comprising calcium phosphate minerals (preferable particle size of 100-2,000 $\mu$) and atelopeptide, reconstituted, crosslinked fibrillocollagen. It purports to be a non-antigenic, biocompatible, composition capable of filling bony defects and promoting bone growth xenogenically.

U.S. Pat. No. 4,789,663 discloses a method of effecting conductive bone repair comprising exposing the defect to fresh bone, and using xenogenic collagen from bone and/or skin, wherein the collagen is enzymatically treated to remove telopeptides, and is artificially cross-linked.

The need to provide a "biological anchor" for implanted prostheses, particularly metallic implants, is well documented in the art. The state of the art of prosthetic implants, disclosed by Specter (1987) *J. Arthroplasty* 2:163-177, generally utilizes porous coated devices, as these coats have been shown to promote cellular ingrowth significantly.

EPO 169,001 (published Jan. 22, 1986, priority Jul. 17, 1984) claims a collagen-coated prosthesis wherein the coat comprises a purified, sterile, non-immunogenic xenogenic collagen preparation from bone or skin. Crosslinking is generally induced to reduce immunogenicity, or occurs as a result of sterilization procedures.

U.S. Pat. No. 4,812,120 discloses a prosthetic device comprising a metal core over which are applied successive polymer layers. The outer layer comprises a biopolymer having protruding collagen fibrils. The protruding fibrils are subject to damage upon implantation of the device.

Efficient in vitro growth of mammalian cells is often limited, by the materials used as the substratum, substrate, or "scaffold" for anchorage-dependent cells. An effective matrix must be physiologically acceptable to the anchorage dependent cells, and it must also provide a large available surface area to which the cells can attach.

GB Pat. No. 2,178,447, published Feb. 11, 1987, claims a fibrous or Porous foam matrix comprising open or closed form fibers, with a pore size on the order of 10-100 μ (matrix height is 50-500 μ). The fiber network is generated as a sheet which must then be modified if different scaffold shapes are desired.

Strand et al. (Biotechnology and Bioengineering, V. 26, 503, 1984) disclose microcarrier beads for use as a matrix for anchorage dependent cells in a matrix perfusion cell culture. Bead materials tested were DEAE or polyacrylamide. Surface area available was 250-300 $cm^2/g$ and required a cell innoculaton of $10^6$ cells/ml.

U.S. Pat. No. 4,725,671 claims collagen fiber membranes suitable for cell culture, comprising soluble atelopeptide collagen fibers that are dried and preferably cross-linked.

The art has sought biocompatible sustained release vehicles with known, reliable "release" rates. Effective carriers must be biocompatible, water-insoluble, capable of trapping or otherwise holding the therapeutic agent of interest, and have a resorption time in vivo that mimics the desired release rate of the agent. Collagen and gelatin are attractive carriers for clinical use, primarily because of their biocompatible and biodegradable properties. (See, for example, EPO 170,979, published Feb. 12, 1986, priority Aug. 07, 1984; and EPO 069,260, published Jan. 12, 1983, priority Jun. 25, 1981.) However, these biopolymers have undesirable crosslinking properties that can make efficient synthesis of appropriate carrier matrices difficult. (EPO 230,647 published Aug. 05, 1987, priority Dec. 27, 1985.)

It is an object of this invention to provide a biocompatible, in vivo biodegradable bone matrix, implantable in a mammalian host with no significant inhibitory immunogenic response. Another object is to provide a biocompatible, in vivo biodegradable matrix capable of combining with an osteoinductive protein to produce endochondral bone formation in mammals, including humans. Still other objects are to provide a superior material for coating implantable prothetic devices, to increase the cellular ingrowth into such devices, to provide a biocompatible, in vivo biodegradable matrix for use as a carrier of sustained-release pharmaceutical compositions, wherein the resorption rate of the matrix can be adjusted to match that of the pharmaceutical agent, and to provide a biocompatible, in vivo biodegradable matrix capable of acting as a scaffold or substratum for anchorage-dependent cells, wherein the surface area available for cell attachment can be adjusted. Yet another object of the invention is to provide a method for the production of such matrix material.

These and other objects and features of the invention will be apparent from the description, drawings, and claims that follow.

SUMMARY OF THE INVENTION

This invention involves a matrix for implantation in a mammalian host comprising biocompatible, mineral-free, insoluble Type-I bone collagen, xenogenic to the host, which, when implanted in the host, is biodegradable. As disclosed herein, the matrix may be combined with osteogenic protein to induce reliably and reproducibly endochondral bone formation in a mammalian body. It may also be used as a surface coat around implantable prosthetic devices to promote cellular ingrowth. It can act as a carrier for the sustained release of various compositions in the mammalian body, and can provide a biocompatible substrate for anchorage-dependent cells.

The development of this matrix material resulted from the discovery of key features required for successful implantation of xenogenic bone matrix and osteogenic protein. Mammalian bone tissue growth requires the influx, proliferation, and differentiation of migratory progenitor cells at the site of the implant. Previous studies indicated that osteogenic devices comprising substantially pure osteogenic protein and demineralized, guanidine-extracted bone matrices must be particulate, with intraparticle interstices dimensioned to permit the influx, proliferation and differentiation of migratory cells. It is also known that osteogenic devices comprising xenogenic bone matrices induce little or no endochondral bone formation in vivo. The inhibitory action of xenogenic matrices was thought to be due to an immunogenic response to protein components still present in the matrix (either the collagen telopeptides or associated non-collagenous glycoproteins.)

It has now been discovered that the overall intraparticle specific surface area (surface area/unit mass) of the matrix itself is also significant for xenogenic implants, even for allogenic implants of certain species. For example, allogenic, subcutaneous implants of demineralized, guanidine-extracted monkey bone matrix with OP is reported not to induce bone formation in the monkey. (Asperberg P., et al (1988) J. Bone Joint Surg. (br) 70-B, 625-627)

Panels A and B of FIGS. 1 and 2 are scanning electron micrographs showing the particle structure of demineralized, guanidine-extracted bone matrix from rat and calf, respectively. As can be seen from the SEMs, there is a significantly greater inherent porosity, or intraparticle surface area, in rat bone matrix over that of bovine bone matrix. It has been discovered that increasing porosity helps entrap protein, and increases in intraparticle surface area can promote osteogenic induction.

Thus, in one aspect, this invention comprises a matrix for implantation in a mammalian host comprising packed particles comprising biodegradable, biocompatible mineral-free, insoluble Type-I bone collagen, xenogenic to the host, the particles being depleted in non-collagenous proteins, having a mean diameter within the range of 70 μm-850 μm, and having an increased intraparticle surface area relative to untreated material.

Another aspect of this invention involves methods of treating demineralized, guanidine extracted matrix particles with a swelling agent so as to increase the intraparticle porosity of the matrix to achieve the desired increase in matrix surface area. The matrix treatments herein described increase the porosity of the matrix particles, thereby altering the integrity of the particles. This alteration has the effect of potentially increasing the resorption time of the matrix in vivo. Thus, one can alter treatment times to vary the matrix resorption rate in vivo (longer treatment times yield faster resorption rates). The swelling agents include acids, for example, trifluoroacetic acid (TFA) and hydrogen fluoride (HF), and organic solvents, for example, dichloromethane (DCM), acetonitrile (ACN) and isopropanol (IP). All these agents are known to have protein denaturation properties and to swell insoluble proteins. Among these, a preferred swelling agent is DCM. The currently most preferred agent is DCM mixed with a small amount, e.g., 0.1%, of TFA.

Another preferred swelling agent is hydrogen fluoride, which is a known deglycosylating agent. Thus, in another aspect the invention provides a matrix for implantation in a mammalian host, comprising deglycosylated Type-I mineral-free bone collagen, xenogenic to the host, and biodegradable and biocompatible in the host. This matrix preferably is in packed particle form. The particles preferably have a mean diameter of 70–850 μm, more preferable 150 μm–420 μm, and have an increased intraparticle surface area relative to untreated material.

Treatment of the matrix with a swelling agent should be followed by an appropriate wash. Xenogenic bone matrices that have been treated with a swelling agent but left unwashed are less osteoinductive when implanted with osteogenic protein in a mammalian host. Panels D and E in FIGS. 1 and 2 show the dramatic effect the wash step has on intraparticle surface area. Currently preferred washes include urea-containing buffer and water, or alternatively, a saline buffer.

Mammalian bone tissue growth requires the influx, proliferation and differentiation of migratory progenitor cells. Accordingly, in one aspect, the invention comprises packed matrix particles, which may be deglycosylated, defining interstices dimensioned to permit the influx, proliferation and differentiation of migratory cells, Preferably having a particle diameter that is in the range of 150-420 μm. In another preferred aspect of the invention, the matrix comprises dispersed protein, e.g., osteogenic protein, and is capable of inducing endochondral bone formation when implanted in a mammalian host. Preferred means of adsorbing the substantially pure osteogenic protein onto the matrix particles include precipitation in cold ethanol from guanidine HCl solution, or incubation in an acetonitrile/trifluoroacetic acid solution or in PBS, followed by lyophilization. The matrix may be shaped to span a non-union fracture or to fill in a defect in bone of a mammalian host.

The biocompatible and in vivo biodegradable nature of the matrix also make it suitable for use as a delivery vehicle for the in vivo sustained release of therapeutic drugs. The increased porosity can increase the matrix's ability to trap and absorb therapeutics. Moreover, it has been discovered that varying the swelling agent treatment times can alter the resorption rate of the matrix in vivo. Thus, this invention provides an easily generated carrier source material of great versatility. In view of this disclosure, those skilled in the art easily can create a carrier matrix having a specific, desired, reliable resorption time. They can then adsorb the agent of interest onto the matrix using one of the methods disclosed herein, or any of the techniques known in the art, to provide a sustained release vehicle with improved reliability in release of the therapeutic compound.

The particulate and porous nature of the material of this invention, along with its biocompatibility in mammalian hosts, permit its use at the interface of an implanted prosthetic device and the surrounding mammalian tissue to promote cellular ingrowth. Moreover, the matrix structure lends itself to increased durability during implantation as compared with collagen fibrils commonly used in such compositions. In view of this disclosure, those skilled in the art easily can create a surface coat for prosthetic devices having a specific, predetermined porosity and increased durability. They can then attach the coat to the prosthetic core using any of the techniques known in the art. See, for example, Cook et al., Clin. Ortho. Rel. Res. No. 232, p. 225, 1988. The matrix further can comprise osteogenic protein if endochondral bone induction is desired.

The nature of the matrix of this invention also makes it a superior substratum for in vitro growth of anchorage-dependent cells. The matrix itself provides a physiologically acceptable surface for cell attachment, and the particle interstices and intraparticle porosity provide significant increases in the surface area available for cell attachment over other known matrices. Moreover, the structure of the matrix of this invention allows one to vary the particle porosity as desired. The cascade of pores present in this matrix promotes efficient nutrient access to cells, and increases the surface area available for cell attachment, thereby lowering the cell inoculant concentration required in a cell perfusion system (See GB No. 2,178,447). In view of this disclosure, one skilled in the art efficiently can create a biocompatible matrix of choice, having a specific, known, desired porosity.

BRIEF DESCRIPTION OF THE DRAWINGS

The foregoing and other objects of this invention, the various features thereof, as well as the invention itself, may be more fully understood from the following description, when read together with accompanying drawings, in which:

FIG. 3 is a bar graph of alkaline phosphatase activity (units/mg protein) as a measure of osteogenesis in the presence of untreated and HF-treated bovine bone matrix.

DETAILED DESCRIPTION

Figure 1A:
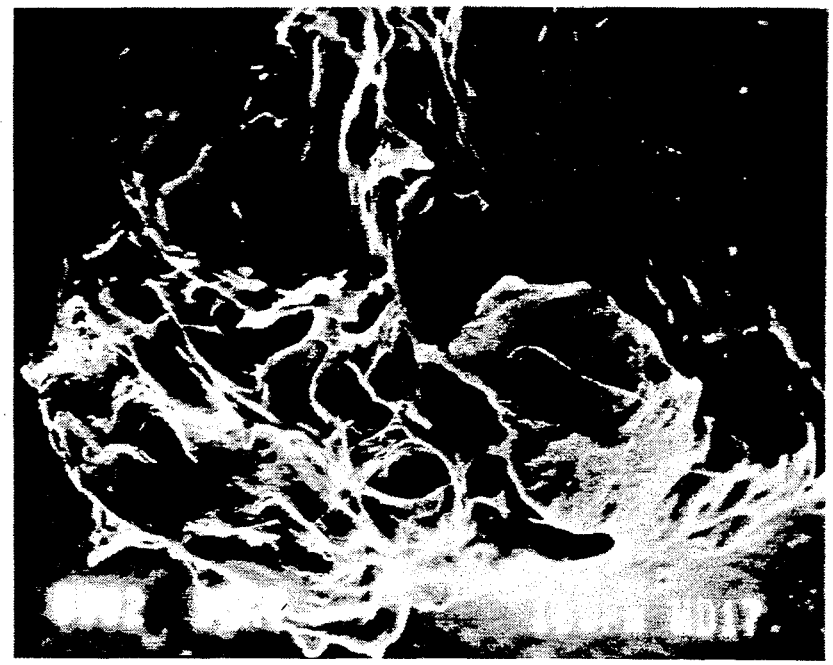
FIGS. 1A through 1E are, respectively, scanning electron micrographs (350X) of: (1A) demineralized, guanidine-extracted rat bone matrix; (1B) demineralized, guanidine-extracted bovine bone matrix; 1C) demineralized, guanidine-extracted bovine bone matrix, further treated with hydrogen fluoride (HF) and washed; (1D) demineralized, guanidine-extracted bovine bone matrix, further treated with dichloromethane (DCM), and washed; (1E) demineralized, guanidine-extracted bovine bone matrix, further treated with dichloromethane (DCM), but unwashed; and (1F) demineralized, guanidine-extracted monkey bone matrix, further treated with hydrogen fluoride, and washed.

Practice of the invention requires the availability of bone, preferably mammalian bone, e.g., bovine. The bone is cleaned, demineralized, reduced to particles of an appropriate size, extracted to remove soluble proteins, sterilized, and otherwise treated as disclosed herein to produce an implantable material useful in a variety of clinical settings.

Matrices of various shapes fabricated from the material of the invention may be implanted surgically for various purposes. Chief among these is to serve as a matrix for bone formation in various orthopedic, periodontal, and reconstructive procedures, as a sustained release carrier, or as a collagenous coating for implants. The matrix may be shaped as desired in anticipation of surgery or shaped by the physician or technician during surgery. Thus, the material may be used for subcutaneous, intraperitoneal, or intramuscular implants; it may be shaped to span a non-union fracture or to fill a bone defect. In bone formation or conduction procedures, the material is slowly absorbed by the body and is replaced by bone in the shape of or very nearly the shape of the implant.

Various growth factors, hormones, enzymes, therapeutic compositions, antibiotics, and other body treating agents may be sorbed onto the carrier material and will be released over time when implanted as the matrix material is slowly absorbed. Thus, various known growth factors such as EGF, PDGF, IGF, FGF, TGF alpha, and TGF beta may be released in vivo. The material can be used to release antibiotics, chemotherapeutic agents, insulin, enzymes, or enzyme inhibitors.

Details of how to make and how to use the materials of the invention are disclosed below.

A. Preparation of Demineralized Bone

Demineralized bovine bone matrix is prepared by previously published procedures (Sampath and Reddi (1983) Proc. Natl. Acad. Sci. USA 80:6591-6595). Bovine diaphyseal bones (age 1-10 days) are obtained from a local slaughterhouse and used fresh. The bones are stripped of muscle and fat, cleaned of periosteum, demarrowed by pressure with cold water, dipped in cold absolute ethanol, and stored at $-20°$ C. They are then dried and fragmented by crushing and pulverized in a large mill. Care is taken to prevent heating by using liquid nitrogen The pulverized bone is milled to a particle size in the range of 70-850 $\mu$m, preferably 150 $\mu$m-420 $\mu$m, and is defatted by two washes of approximately two hours duration with three volumes of chloroform and methanol (3:1). The particulate bone is then washed with one volume of absolute ethanol and dried over one volume of anhydrous ether yielding defatted bone powder. The defatted bone powder is then demineralized by four successive treatments with 10 volumes of 0.5 N HCl at 4° C. for 40 min. Finally, neutralizing washes are done on the demineralized bone powder with a large volume of water.

B. Guanidine Extraction

Demineralized bone matrix thus prepared is extracted with 5 volumes of 4 M guanidine-HCl, 50 mM Tris-HCl, pH 7.0 for 16 hr. at 4° C. The suspension is filtered. The insoluble material is collected and used to fabricate the matrix. The material is mostly collagenous in nature. It is devoid of osteogenic or chondrogenic activity.

C. Xenooenic-Soecific Treatments

Cl. Hydrogen Fluoride

The major component of all bone matrices is Type-I collagen. In addition to collagen, demineralized bone extracted as disclosed above includes noncollagenous proteins which may account for 5% of its mass. Many noncollagenous components of bone matrix are glycoproteins. In a xenogenic matrix, these glycoproteins may present themselves as potent antigens by virtue of their carbohydrate content and may constitute immunogenic and/or inhibitory components. A collagenous bone matrix may be used for xenogenic implants if one first treats the immunogenic and inhibitory components from the matrix with HF. Hydrogen fluoride is a known deglycosylating agent, and as a strong acid and swelling agent, also alters intraparticle surface structure.

Bovine bone residue prepared as described above is sieved, and particles of the appropriate size are collected. The sample is dried in vacuo over $P_2O_5$, transferred to the reaction vessel, and exposed to anhydrous hydrogen fluoride (10-20 ml/g of matrix) by distillation onto the sample at $-70°$ C. The vessel is allowed to warm to 0° C. and the reaction mixture is stirred at this temperature for 120 min. After evaporation of the HF in vacuo the residue is dried thoroughly in vacuo over KOH pellets to remove any remaining traces of acid. Extent of deglycosylation can be determined from carbohydrate analysis of matrix samples taken before and after treatment with HF, after washing the samples appropriately to remove non-covalently bound carbohydrates. SDS extracted protein from HF treated material is negative for carbohydrate as determined by Con A blotting.

The deglycosylated bone matrix is next treated as set forth below:

1) suspend in TBS (Tris-buffered saline) 1 g/200 ml, and stir at 4° C. for 2 hrs; or in 6 M urea, 50 mM Tris-HCl, 500 mM NaCl, pH 7.0 (UTBS) and stir at room temperature (RT) for 30 min;
2) centrifuge and wash with TBS or UTBS; and
3) centrifuge; discard supernatant; water wash residue; and then lyophilize.

C2. Trifluoroacetic acid

Like hydrogen fluoride, trifluoroacetic acid (TFA) is known to cause swelling of proteins. However, it does not effect deglycosylation.

Bovine bone residue, prepared as described above is sieved, and particles of the appropriate size are extracted with various percentage (1.0% to 100%) of trifluoroacetic acid in water (v/v) at 0° C. or RT for 1-2 hours with constant stirring. The treated matrix is filtered, lyophilized or washed with water/salt and then lyophilized.

C3. Dichloromethane

Dichloromethane (DCM) is an organic solvent capable of denaturing proteins without affecting their primary structure. It is a common reagent in automated peptide synthesis, and is used in washing steps to remove unwanted components. DCM does not cause deglycosylation.

Bovine bone residue particles of the appropriate size prepared as described above are incubated for one or two hours at 0° C., and also at RT for the same duration. After the treatment, the matrix is washed with the standard 6 M urea containing buffer, or water alone. Alternatively, the matrix is treated with DCM many times (X3) with short washes (20 min. each) with no incubation.

C4. Acetonitrile

Acetonitrile (ACN) is an organic solvent, capable of denaturing proteins without affecting their primary structure. It is a common reagent in high performance liquid chromatography, and is used to elute proteins from silica based columns by perturbing hydrophobic interactions. Acetonitrile does not cause deglycosylation.

Bovine bone residue particles of the appropriate size prepared as described above are treated with 100% acetonitrile (1.0 g/30ml) at room temperature for one to two hours with constant stirring. The treated matrix is then water washed, or washed with urea buffer, or 4M NaCl, and lyophilized.

C5. Isopropanol

Isopropanol also is an organic solvent capable of denaturing proteins without affecting their primary structure. It is a common reagent used to elute proteins from silica HPLC columns. Isopropanol does not cause deglycosylation.

Bovine bone residue particles of the appropriate size prepared as described above are treated with 100% isopropanol (1.0 g/30 ml) at room temperature for one to two hours with constant stirring. The treated matrix is then water washed, or washed with urea buffer or 4M NaCl before being lyophilized.

C6. Combinations of Reagents

Figure 4:
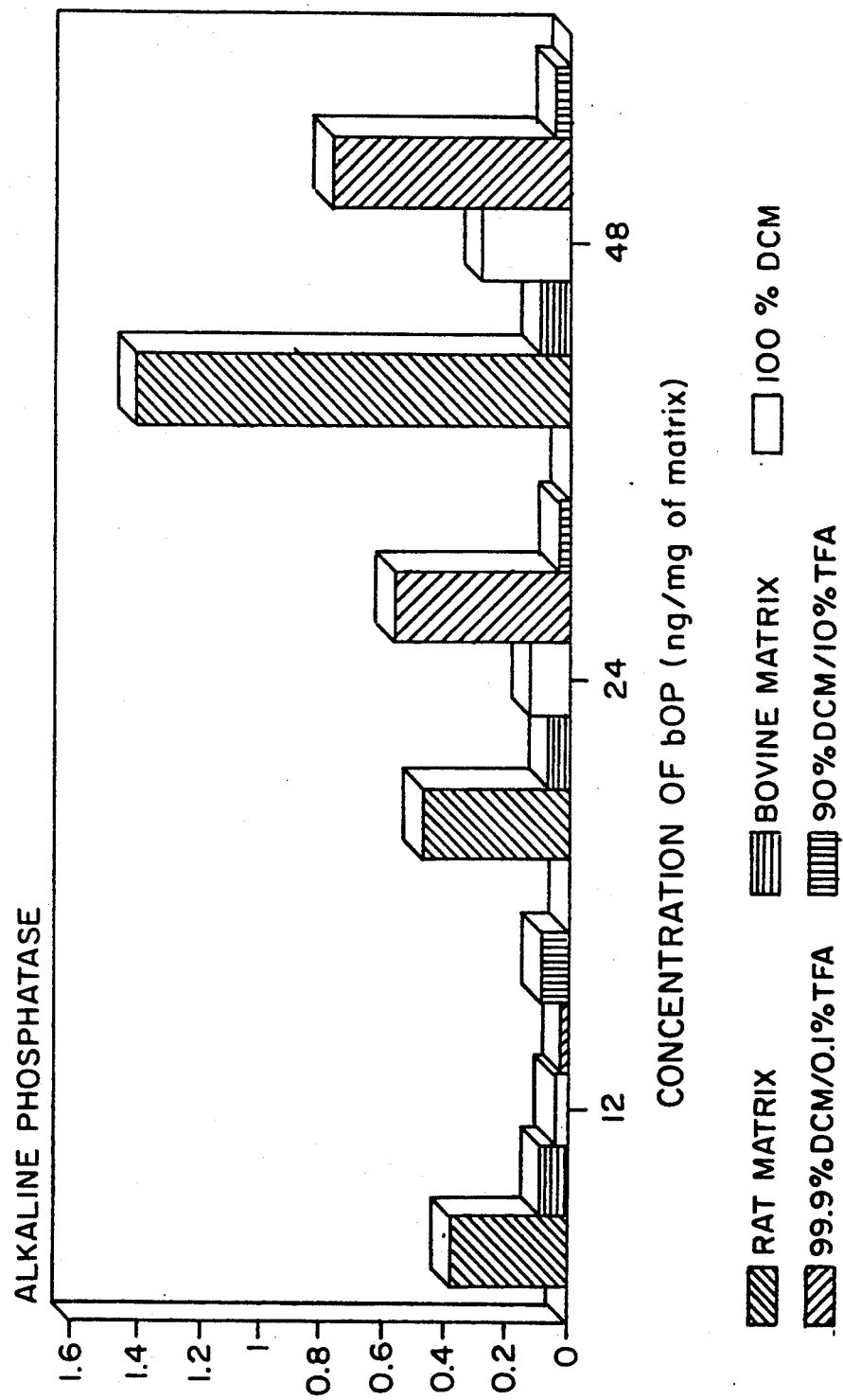
FIG. 4 is a bar graph of alkaline phosphatase activity as a measure of osteogenesis in the presence of variously treated bovine matrix materials using DCM and DCM/TFA, and differing amounts of osteogenic protein.

Separate bovine bone particle samples are treated with dichloromethane, or acetonitrile, and isopropanol, each of which contained 0.1% trifluoroacetic acid. The optimal conditions for the treatment are incubation with solvent/acid mixture at 0° C. or RT for one to two hours with constant stirring. The treated matrix is then lyophilized without wash. Alternately, the treated matrices are washed with water or 4 M salt before lyophilization. FIG. 4 illustrates the effectiveness of these various treatments in converting bovine matrix to a material useful as a bone formation matrix in rat. Further particulars of the evaluation procedures are set forth below.

Treatment as set forth above in the swelling agents and other reagents is effective to assure that the material is free of pathogens prior to implantation.

The material is a fine powder, insoluble in water, comprising nonadherent particles. It may be used simply by packing into the volume where new bone growth is desired, held in place by surrounding tissue. Then, immobilizing the region is sufficient to permit osteogenesis. Alternatively, the powder may be encapsulated in, e.g., a gelatin or polylactic acid coating, which is adsorbed readily by the body. The powder may be shaped to a volume of given dimensions and held in that shape by interadhering the particles using, for example, soluble, species biocompatible collagen.

II. IN VIVO RAT BIOASSAY

The functioning of the various xenogenic matrices can be evaluated with an in vivo rat bioassay. Studies in rats show the osteogenic effect in an appropriate matrix to be dependent on the dose of osteogenic protein dispersed in the matrix. No activity is observed if the matrix is implanted alone. Demineralized, guanidine extracted xenogenic bone matrix materials of the type described in the literature are ineffective as a carrier, fail to induce bone, and produce an inflammatory and immunological response when implanted unless treated as disclosed above. The following sets forth various procedures for preparing osteogenic devices from control and matrix materials prepared as set forth above, and for evaluating their xenogenic utility.

A. Fabrication of Osteogenic Device

The osteogenic protein may be obtained using the methods disclosed in U.S. Pat. application No. 179,406 filed Apr. 8, 1988; PCT U.S. application Ser. No. 89/01469 (entitled Biosynthetic Osteogenic Proteins and Osteogenic Devices Containing Them), and PCT U.S. application Ser. No. 89/01453, (entitled Osteogenic Devices). Both PCT applications were filed Apr. 7, 1989. Alternatively, extracts rich in osteogenic protein useful in fabricating devices may be obtained as disclosed in U.S. Pat. No. 4,294,753 to Urist. The disclosure of these documents is incorporated herein by reference.

A1. Ethanol Precipitation

Matrix is added to osteogenic protein dissolved in guanidine-HCl. Samples are vortexed and incubated at a low temperature. Samples are then further vortexed. Cold absolute ethanol is added to the mixture which is then stirred and incubated. After centrifugation (microfuge, high speed) the supernatant is discarded. The matrix is washed with cold concentrated ethanol in water and then lyophilized.

A2. Acetonitrile Trifluoroacetic Acid Lyophilization

In this procedure, osteogenic protein in an acetonitrile trifluroacetic acid (ACN/TFA) solution was added to the carrier material. Samples were vigorously vortexed many times and then lyophilized. Osteogenic protein was added in varying concentrations, and at several levels of purity. This method is currently preferred.

A3. Urea Lyophilization

For those osteogenic proteins that are prepared in urea buffer, the protein is mixed with the matrix material, vortexed many times, and then lyophilized. The lyophilized material may be used "as is" for implants.

These procedures also can be used to adsorb other active therapeutic drugs, hormones, and various bioactive species for sustained release purposes.

B. Implantation

The bioassay for bone induction as described by Sampath and Reddi (Proc. Natl. Acad. Sci. USA (1983) 80:6591-6595), herein incorporated by reference, may be used to monitor endochondral bone differentiation activity. This assay consists of implanting the bovine test samples xenogenically in subcutaneous sites in recipient rats under ether anesthesia. Male Long-Evans rats, aged 28-32 days, were used. A vertical incision (1 cm) is made under sterile conditions in the skin over the thoracic region, and a pocket is prepared by blunt dissection. Approximately 25 mg of the test sample is implanted deep into the pocket and the incision is closed with a metallic skin clip. The day of implantation is designated as day of the experiment. Implants were removed on day 12. The heterotropic site allows for the study of bone induction without the possible ambiguities resulting from the use of orthotopic sites.

C. Cellular Events

Successful implants exhibit a controlled progression through the stages of matrix induced endochondral bone development including: (1) transient infiltration by polymorphonuclear leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoblastic and bone remodeling and dissolution of the implanted matrix on days twelve to eighteen; and (8) hematopoietic bone marrow differentiation in the ossicle on day twenty-one. The results show that the shape of the new bone conforms to the shape of the implanted matrix.

D. Histological Evaluation

Histological sectioning and staining is preferred to determine the extent of osteogenesis in the implants. Implants are fixed in Bouins Solution, embedded in paraffin, and cut into 6-8 μm sections. Staining with toluidine blue or hemotoxylin/eosin demonstrates clearly the ultimate development of endochondral bone. Twelve day implants are usually sufficient to determine whether the implants contain newly induced bone.

E. Biological Markers

Alkaline phosphatase activity may be used as a marker for osteogenesis. The enzyme activity may be determined spectrophotometrically after homogenization of the implant. The activity peaks at 9–10 days in vivo and thereafter slowly declines. Implants showing no bone development by histology have little or no alkaline phosphatase activity under these assay conditions. The assay is useful for quantitation and obtaining an estimate of bone formation quickly after the implants are removed from the rat. Alternatively, the amount of bone formation can be determined by measuring the calcium content of the implant.

RESULTS

The histological evaluation of implants made using HF- or DCM-treated bone matrices is given in Table 1 and in FIG. 3. The osteogenic protein (OP) used in these experiments was isolated by the method disclosed in U.S. Pat. application No. 179,406. Experiments were performed using either moderately pure protein (See Part A in table, 10–20% pure) or highly pure protein (See Part B). The results demonstrate unequivocally that xenogenic implants of collagenous bovine bone matrix treated as disclosed herein induces successful endochondral bone formation.

TABLE 1

Osteogenic Activity in rat of HF- and DCM-treated bovine bone matrix, rat matrix, and untreated bovine matrix (25 mg matarix material per implant):

| | Rat (untreated) | Bovine (untreated) | HF | DCM |
|---|---|---|---|---|
| A. (10-20% pure OP): | | | | |
| μg OP | | | | |
| 1.8 | + | − | − | − |
| 3.8 | ++ | − | + | + |
| 7.5 | +++ | +/− | ++ | +++ |
| B. (Purified OP:) | | | | |
| ng OP | | | | |
| 250 | ++ | − | +/− | + |
| 500 | +++ | − | + | ++ |
| 1000 | +++ | +/− | ++ | +++ |

Histology score:
− no bone formation
+ slight bone formation
++ moderate bone formation
+++ extensive bone formation FIG. 3 shows the effect of HF treatment on bone formation in xenogenic rat implants, as measured by specific activity of alkaline phosphatase. It is evident from these results that osteogenic devices using an HF treated xenogenic bone matrix induce bone, whereas devices using an untreated matrix do not.

FIG. 4 illustrates the osteoinductive effect of water washed matrix treated with nanogram quantities of purified OP, as indicated by specific activity of alkaline phosphatase, for allogenic rat matrix and xenogenic bovine matrix untreated, treated with DCM alone, 99.9% DCM plus 0.1% TFA, and 90% DCM plus 10% TFA. As illustrated, DCM with low acidified concentrations of acid enhances bone formation.

Figure 2A:
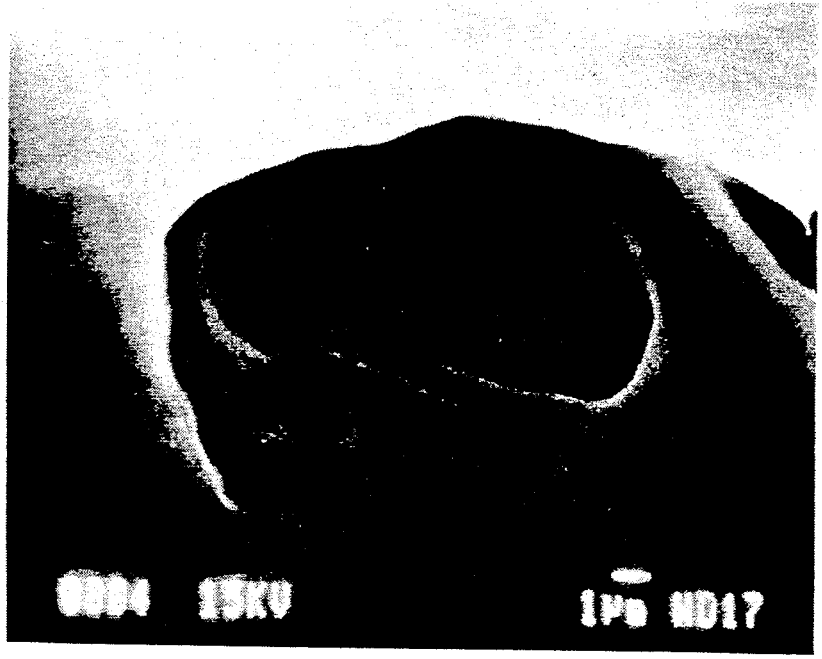
FIGS. 2A through 2E are, respectively, SEMs (5000x) of: (2A) demineralized, guanidine-extracted rat bone matrix; (2B) demineralized, guanidine-extracted bovine bone matrix; (2C) demineralized, guanidine-extracted bovine bone matrix, further treated with hydrogen fluoride, and washed; (2D) demineralized, guanidine-extracted bovine bone matrix, further treated with dichloromethane, and washed; and (2E) demineralized, guanidine-extracted bovine bone matrix, further treated with dichloromethane, but unwashed.
Figure 1B:
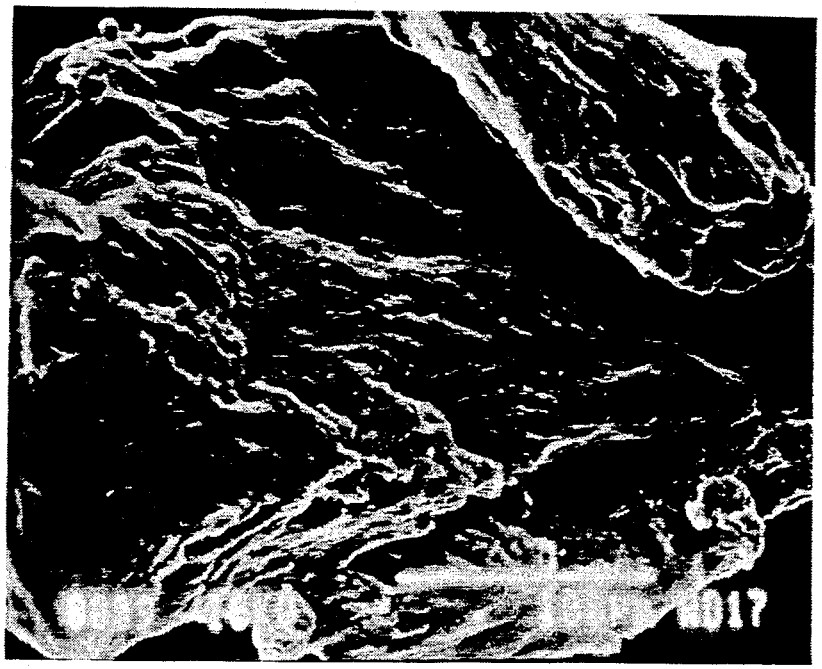
Figure 2B:
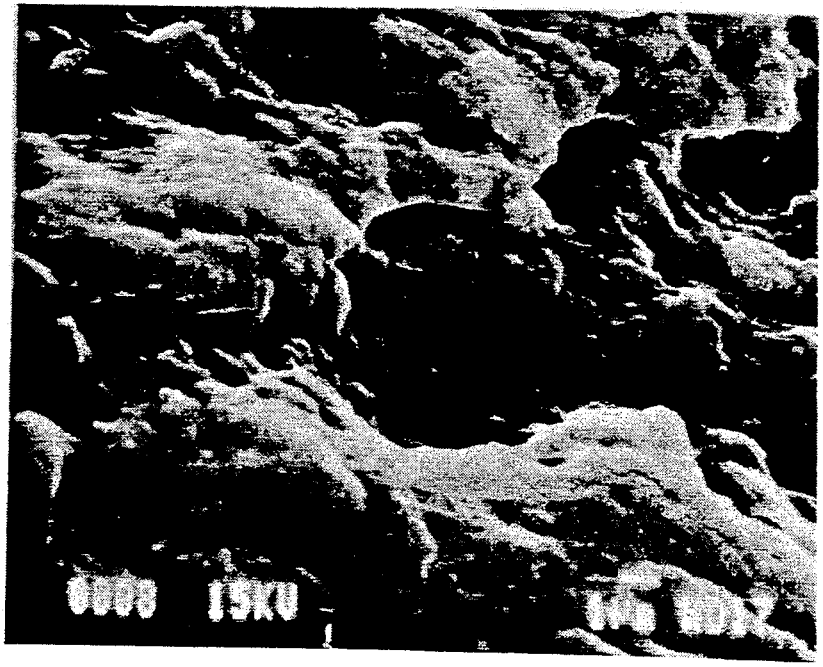
Figure 1C:
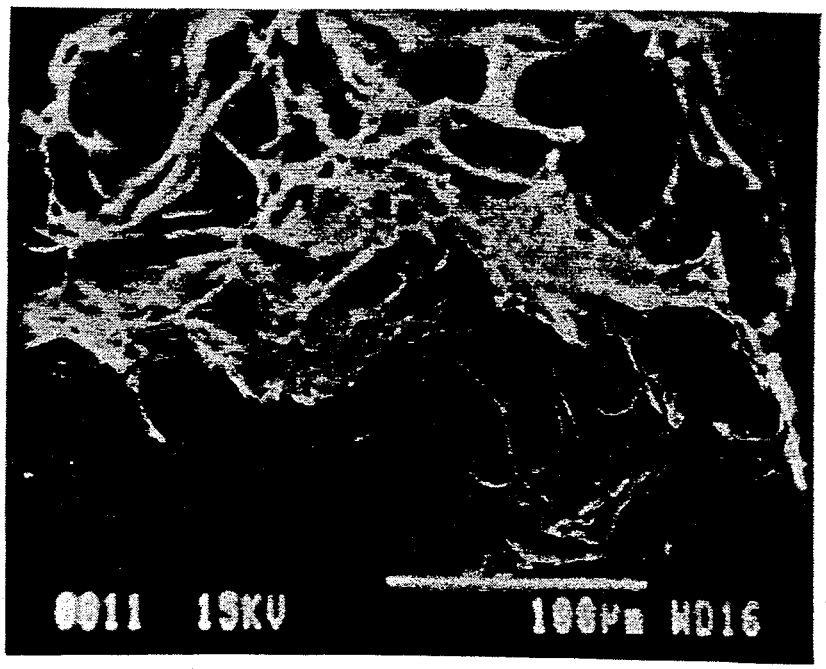
Figure 2C:
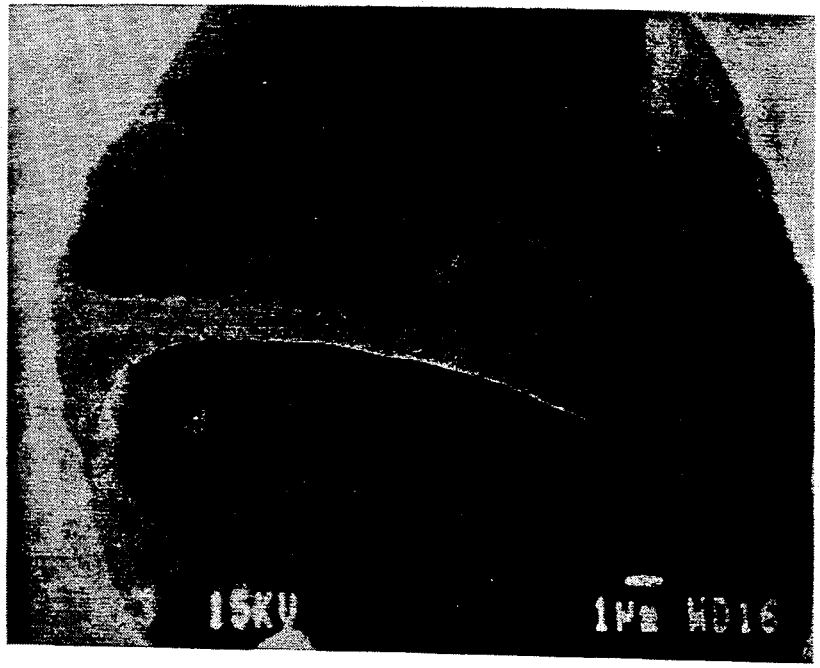
Figure 1D:
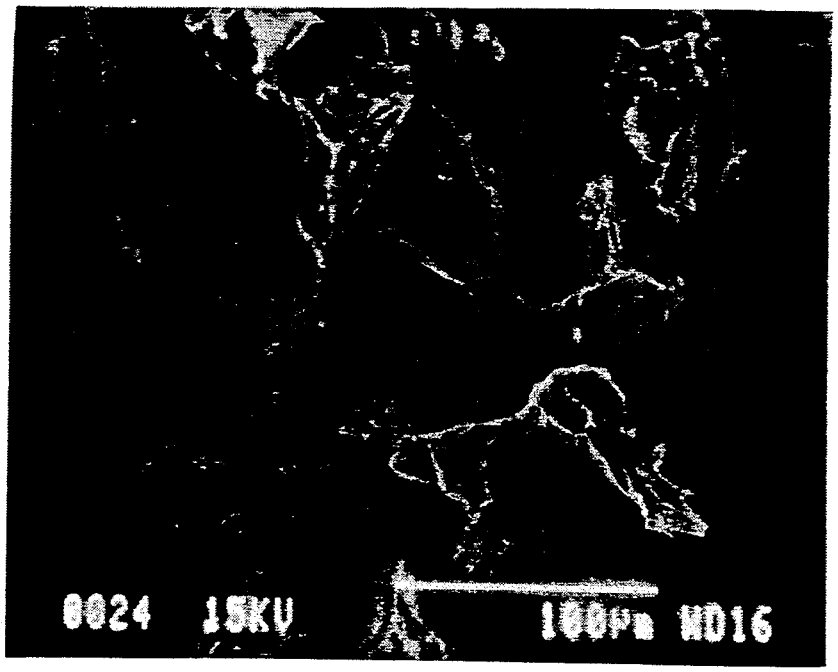
Figure 2D:
Figure 1E:
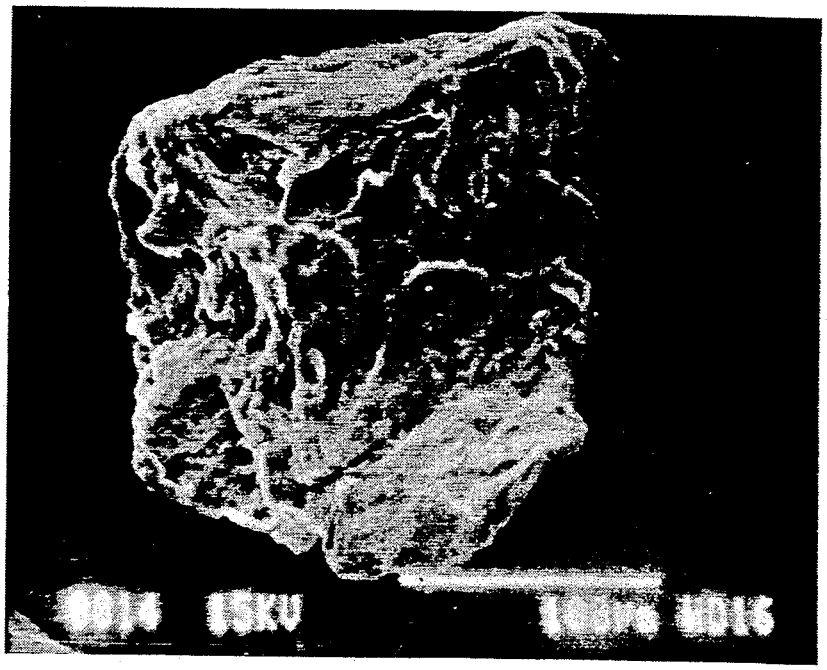
Figure 2E:
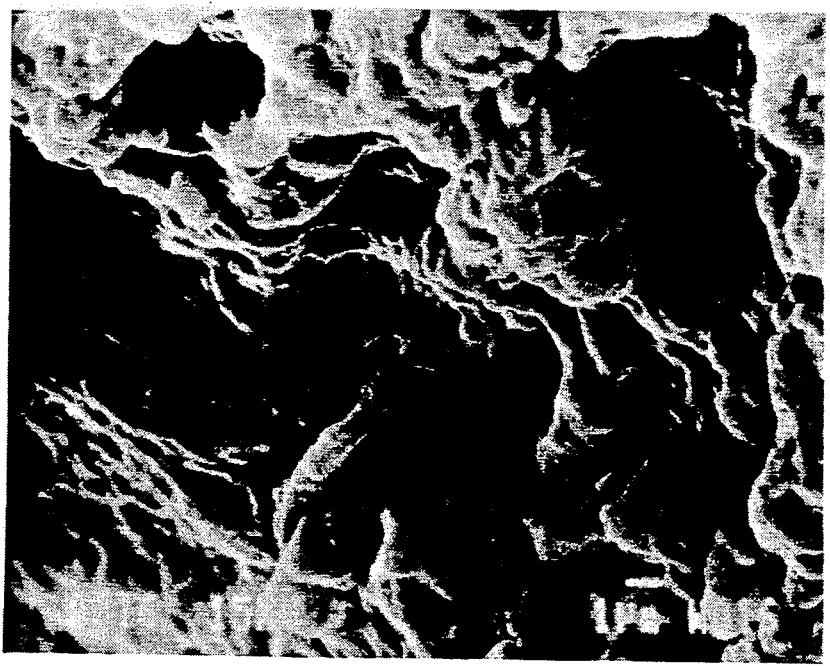
Figure 1F:
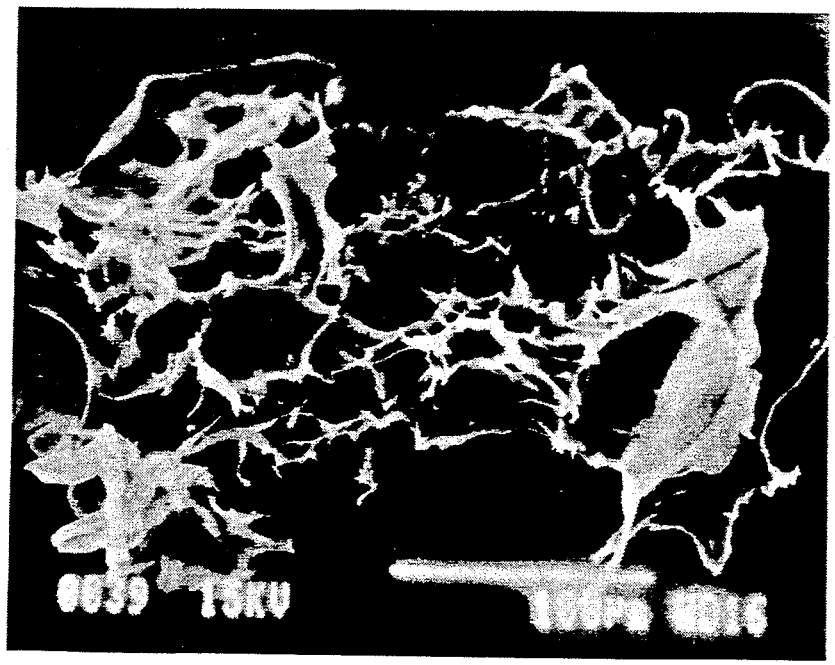

The foregoing treatment protocols generically serve to remove extraneous soluble proteins from the bone collagen and to increase its intraparticle surface area. While both these aspects may be important to production of an optimal matrix, the utility of the material of the invention in its use as a osteogenic implant is believed to be dependent in part on increases in intraparticle surface area or porosity. The basis for this conclusion is apparent from a review and comparison of FIGS. 1A through 2E. Untreated rat matrix, shown in FIGS. 1A and 2A, is active in rats and has an obvious, open pore, high surface area structure. The untreated bovine matrix of FIG. 1B and 2B has a lower surface area and is inactive in rats. However, treatment of the bovine collagen with HF (FIGS. 1C and 2C) or with DCM (FIG. 1D and 2D) produces an open pore, high surface area structure which is active xenogenically. FIGS. 1E and 2E show the appearance of bovine matrix particles when treated with DCM but omitting the washing step. As illustrated, omission of the wash produces a low surface are structure similar to untreated bovine collagen, and results in an inactive matrix material. FIG. 1F shows the structure of monkey bone collagen after treatment with HF as disclosed above. The bone particles may be used xenogenically to induce bone. Demineralized, guarnidine extracted monkey bone reportedly is ineffective as a osteogenic matrix, even as an allogneic implant.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A matrix for implantation in a mammalian host comprising:
   a) biodegradable, biocompatible, mineral-free Type-I insoluble bone collagen particles, xenogenic to said host and having intraparticle pores, said particles being depleted in noncollagenous protein, having a mean diameter within the range of 70 μm to 850 μm, and an intraparticle surface area greater than the surface are of native demineralized bone powder, and
   b) an osteogenic protein adsorbed onto a surface thereof.

2. A matrix for implantation in a mammalian host comprising:
   a) biodegradable, biocompatible, mineral-free Type-I insoluble bone collagen particles, xenogenic to said host and having intraparticle pores, said particles being depleted in noncollagenous protein, having a mean diameter within the range of 70 μm to 850 μm, and an intraparticle surface area greater than the surface area of native demineralized bone powder, and
   b) a therapeutic drug adsorbed onto a surface thereof for sustained release in said mammalian host.

3. The matrix of claim 1, or 2 comprising packed particles.

4. The matrix of claim 3 wherein said particles have a mean diameter within the range of 150 μm to 420 μm.

5. The matrix of claim 3 wherein said particles are deglycosylated.

6. The matrix of claim 3 wherein the particles define interstices dimensioned to permit influx, proliferation and differentiation of migratory cells from the body of said mammalian host.

7. The matrix of claim 3 wherein said matrix is shaped to span a non-union fracture in said mammalian host.

8. The matrix of claim 3 wherein said particles are incubated with a swelling agent followed by washing to remove soluble components.

9. The matrix of claim 8 wherein said swelling agent is an organic protein denaturant.

10. The matrix of claim 8 wherein said swelling agent is dichloromethane.

11. The matrix of claim 8 wherein said swelling agent is hydrogen fluoride.

12. The matrix of claim 8 wherein said swelling agent is trifluoroacetic acid.

13. The matrix of claim 8 wherein said swelling agent is dichloromethane, acetonitrile, or isopropanol mixed with 0.1%–10% trifluoroacetic acid.

14. The matrix of claim 8 wherein said swelling agent is isopropanol.

15. The matrix of claim 8 wherein said swelling agent is acetonitrile.

* * * * *